US012637648B2

(12) United States Patent
Li et al.

(10) Patent No.: US 12,637,648 B2
(45) Date of Patent: May 26, 2026

(54) METHOD FOR MANUFACTURING NANOSTRUCTURE AND NANOSTRUCTURE

(71) Applicant: INSTITUTE OF MICROELECTRONICS, CHINESE ACADEMY OF SCIENCES, Beijing (CN)

(72) Inventors: Junjie Li, Beijing (CN); Na Zhou, Beijing (CN); Enxu Liu, Beijing (CN); Jianfeng Gao, Beijing (CN); Junfeng Li, Beijing (CN); Jun Luo, Beijing (CN); Wenwu Wang, Beijing (CN)

(73) Assignee: INSTITUTE OF MICROELECTRONICS, CHINESE ACADEMY OF SCIENCES, Beijing (CN)

( * ) Notice: Subject to any disclaimer, the term of this patent is extended or adjusted under 35 U.S.C. 154(b) by 210 days.

(21) Appl. No.: 18/529,820

(22) Filed: Dec. 5, 2023

(65) Prior Publication Data

US 2024/0191168 A1    Jun. 13, 2024

(30) Foreign Application Priority Data

Dec. 8, 2022    (CN) .......................... 202211576202.1

(51) Int. Cl.
*C12M 1/12*      (2006.01)
*G03F 7/00*      (2006.01)
(52) U.S. Cl.
CPC ......... *C12M 25/04* (2013.01); *G03F 7/70383* (2013.01)
(58) Field of Classification Search
CPC ......... H01L 21/30604; H01L 21/31056; H10P 50/24; H10P 50/28; H10P 50/642
See application file for complete search history.

(56) References Cited

U.S. PATENT DOCUMENTS

| | | | | |
|---|---|---|---|---|
| 7,989,307 | B2 * | 8/2011 | Parekh ................. | H10B 12/053 |
| | | | | 438/424 |
| 2011/0048947 | A1 | 3/2011 | Petronis et al. | |
| 2012/0040512 | A1 | 2/2012 | Li et al. | |
| 2023/0411456 | A1 * | 12/2023 | More ................. | H10D 30/6735 |

FOREIGN PATENT DOCUMENTS

| | | |
|---|---|---|
| CN | 108807149 A | 11/2018 |
| CN | 110164762 A | 8/2019 |
| CN | 111569963 A | 8/2020 |
| KR | 20170063086 A | 6/2017 |

OTHER PUBLICATIONS

First Office Action issued on Jan. 7, 2025 from CNIPA for Chinese patent Application No. 202211576202.1, 10 pgs.

* cited by examiner

*Primary Examiner* — Thomas T Pham
(74) *Attorney, Agent, or Firm* — Kinney & Lange, P.A.

(57) ABSTRACT

A method for manufacturing a nanostructure and a nanostructure are disclosed. The method for manufacturing the nanostructure includes first alternately and periodically stacking a first material layer and a second material layer on a substrate to form a stacked layer, then forming a slot pattern on an upper surface of the stacked layer and etching the stacked layer to an upper surface of the substrate to transfer the slot pattern to the stacked layer, filling the slot pattern in the stacked layer with a molding material, and removing the first material layer or the second material layer left in the stacked layer, so as to form nanopores arranged in an array in the stacked layer.

9 Claims, 5 Drawing Sheets

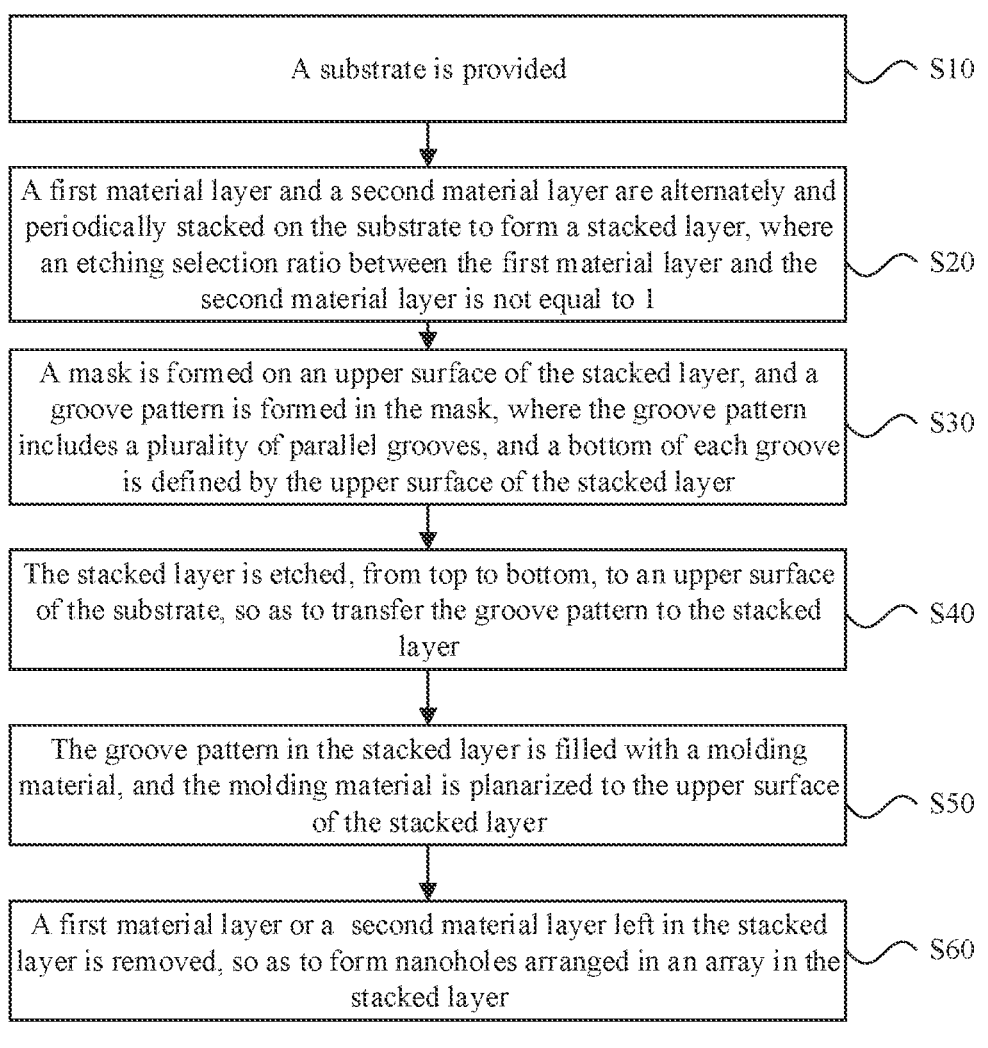

| | |
|---|---|
| A substrate is provided | S10 |
| A first material layer and a second material layer are alternately and periodically stacked on the substrate to form a stacked layer, where an etching selection ratio between the first material layer and the second material layer is not equal to 1 | S20 |
| A mask is formed on an upper surface of the stacked layer, and a groove pattern is formed in the mask, where the groove pattern includes a plurality of parallel grooves, and a bottom of each groove is defined by the upper surface of the stacked layer | S30 |
| The stacked layer is etched, from top to bottom, to an upper surface of the substrate, so as to transfer the groove pattern to the stacked layer | S40 |
| The groove pattern in the stacked layer is filled with a molding material, and the molding material is planarized to the upper surface of the stacked layer | S50 |
| A first material layer or a second material layer left in the stacked layer is removed, so as to form nanoholes arranged in an array in the stacked layer | S60 |

FIG. 1

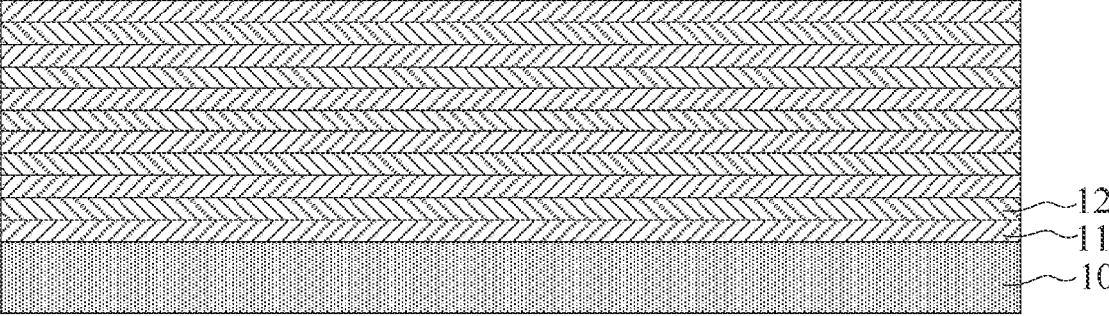

FIG. 2

METHOD FOR MANUFACTURING NANOSTRUCTURE AND NANOSTRUCTURE

CROSS-REFERENCE TO RELATED APPLICATIONS

This application claims benefit of the filing date of Chinese Patent Application No. 202211576202.1 filed on Dec. 8, 2022, the disclosure of which is hereby incorporated in its entirety by reference.

TECHNICAL FIELD

The present disclosure relates to a field of micro/nano pore technology, and in particular, to a method for manufacturing a nanostructure and a nanostructure.

BACKGROUND

Micro/nano pore channel materials have very wide application values in the field of biology/medicine, such as DNA sequencing, macromolecule detection, nanotemplates, drug transmission, and so on. At present, there are two main solutions for manufacturing micro-nano sieve pores. A first solution uses chemical synthesis materials, such as a porous metal oxide film formed through anodization and chemical corrosion. Disadvantages of this solution are that it is difficult to control the sizes of the pores to be uniform, and the pores are also difficult to distribute in a regular array. A second solution uses an integrated circuit processing method combined with a photolithography technique and etching technique, with which it is possible to manufacture pores with consistent sizes of holes and arranged in a geometrically regular array, but diameters and density of the pores are limited by the photolithography technique and etching technique.

SUMMARY

The present disclosure provides a method for manufacturing a nanostructure and a nanostructure. It is possible to not only ensure that nanopores are arranged in a regular geometric array, but also control diameters of nanopores and a density of the nanopores by adjusting a spacing b slot of a slot pattern and a thickness of the first material layer and a thickness of the second material layer.

In an aspect, the present disclosure provides a method for manufacturing a nanostructure, including:

providing a substrate;

alternately and periodically stacking a first material layer and a second material layer on the substrate to form a stacked layer, where an etching selection ratio between the first material layer and the second material layer is not equal to 1;

forming a mask on an upper surface of the stacked layer and forming a slot pattern in the mask, where the slot pattern includes a plurality of parallel slots, and each slot has the upper surface of the stacked layer as a bottom;

etching the stacked layer from top to bottom, to an upper surface of the substrate, so as to transfer the slot pattern to the stacked layer;

filling the slot pattern in the stacked layer with a molding material, and planarizing the molding material to the upper surface of the stacked layer;

removing the first material layer or the second material layer left in the stacked layer, so as to form nanopores arranged in an array in the stacked layer.

In the above solution, a stacked layer is formed by alternately and periodically stacking the first material layer and the second material layer on the substrate. Then, a slot pattern is formed on an upper surface of the stacked layer and the stacked layer is etched to an upper surface of the substrate, so as to transfer the slot pattern to the stacked layer. Next, the slot pattern in the stacked layer is filled with a molding material. The first material layer or the second material layer left in the stacked layer is removed, so as to form the nanopores arranged in an array in the stacked layer. Compared with existing methods, it is possible to not only ensure that the nanopores are arranged in a regular geometric array, but also control a diameter of the nanopore and a density of the nanopores by adjusting a spacing between slots of the slot pattern, a thickness of the first material layer and a thickness of the second material layer.

In a specific embodiment, the molding material is silicon dioxide or aluminum oxide.

In a specific embodiment, a material of the first material layer is silicon germanium material, and a material of the second material layer is silicon.

In a specific embodiment, a concentration of germanium in the silicon germanium material is within a range of 5% to 100%, so that the first material layer and the second material layer have a large etching selectivity ratio.

In a specific embodiment, a thickness of the first material layer is between 0.5 nm and 100 nm, a thickness of the second material layer is between 0.5 nm and 100 nm, and a total number of the first material layer and second material layer included in the stacked layer is within a range of 2 layers to 1000 layers.

In a specific embodiment, the removing the first material layer or the second material layer left in the stacked layer, so as to form nanopores arranged in an array in the stacked layer, including: removing the first material layer or the second material layer left in the stacked layer by using a gas etching method or a liquid etching method.

In a specific embodiment, when removing the first material layer or the second material layer left in the stacked layer by using the gas etching method, an etching gas used in the gas etching is a mixed gas of $CIF_3$ and $CF_4/O_2/He$, or a mixed gas of $NF_3/NH_3/O_2$, so as to improve an efficiency and effectiveness of gas etching. When removing the first material layer or the second material layer left in the stacked layer by using the liquid etching method, an etching liquid used in the liquid etching is a mixed liquid of $CH_3COOH/H_2O_2/HF$.

In a specific embodiment, the forming a mask on an upper surface of the stacked layer and forming a slot pattern in the mask, includes: forming the mask on the upper surface of the stacked layer and forming the slot pattern in the mask by using a direct photolithography patterning process, a spacer patterning process or a photolithography plus spacer patterning process.

In a specific embodiment, the forming the mask on the upper surface of the stacked layer and forming the slot pattern in the mask by using a photolithography plus spacer patterning process, includes:

depositing a transition mask on the upper surface of the stacked layer;

forming a transition slot pattern in the transition mask by using a direct photolithography patterning process, where the transition slot pattern includes a plurality of parallel transition slots, and each transition slot has the upper surface of the stacked layer as a bottom;

depositing a mask on a sidewall of the transition slot pattern and a protruded surface between adjacent transition slots;

etching off the mask on the protruded surface between the adjacent transition slots by using an anisotropic etching process;

removing the transition mask left such that the mask left serves as a spacer, where a slot of the slot pattern is formed between two adjacent spacers.

In another second aspect, the present disclosure also provides a nanostructure. The nanostructure is manufactured by using any of the above methods for manufacturing a nanostructure. A stacked layer is formed by alternately and periodically stacking the first material layer and the second material layer on the substrate. Then, a slot pattern is formed on an upper surface of the stacked layer and the stacked layer is etched to an upper surface of the substrate, so as to transfer the slot pattern to the stacked layer. Next, the slot pattern in the stacked layer is filled with a molding material. The first material layer or the second material layer left in the stacked layer is removed, so as to form nanopores arranged in an array in the stacked layer. Compared with existing methods, it is possible to not only ensure that the nanopores are arranged in a regular geometric array, but also control diameters of the nanopores and a density of the nanopores by adjusting a spacing between slots of the slot pattern, a thickness of the first material layer and a thickness of the second material layer.

BRIEF DESCRIPTION OF THE DRAWINGS

FIG. 1 shows a flowchart of a method for manufacturing a nanostructure provided by an embodiment of the present disclosure; and FIG. 2 to FIG. 12 show schematic structural diagrams of a section in respective steps of a method for manufacturing a nanostructure provided by an embodiment of the present disclosure.

REFERENCES SIGNS

Figure 3:
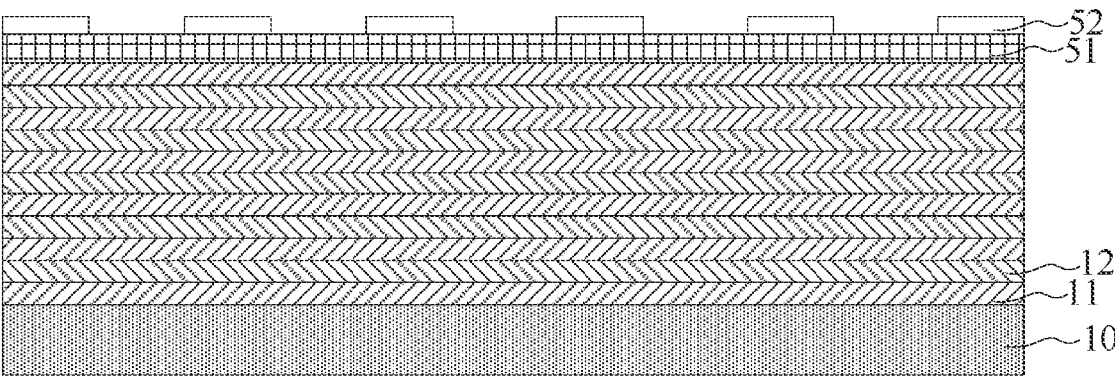
Figure 4:
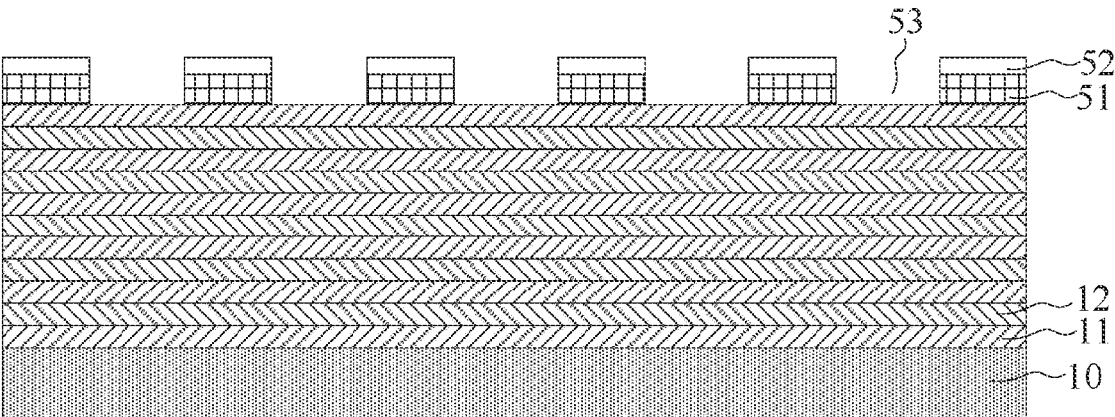
Figure 5:
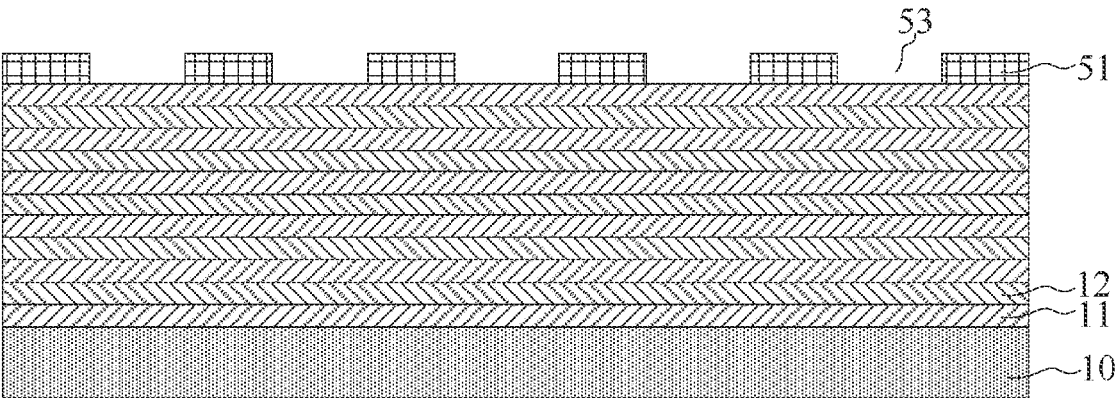
Figure 6:
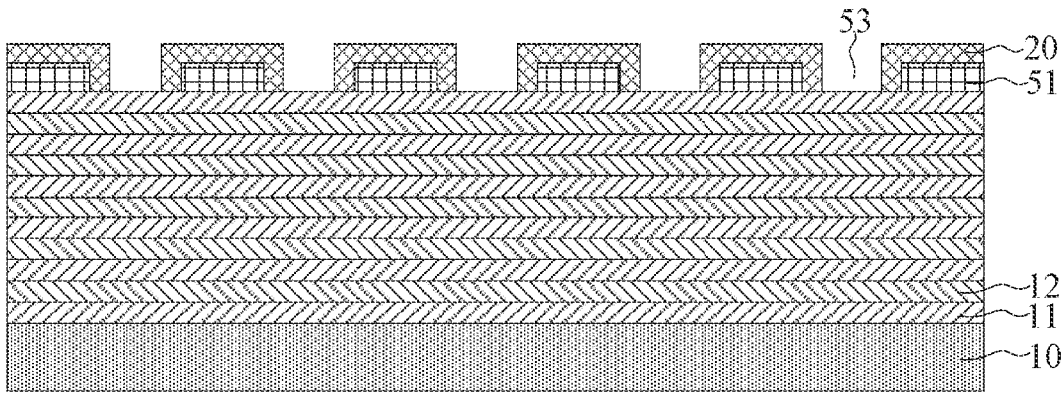
Figure 7:
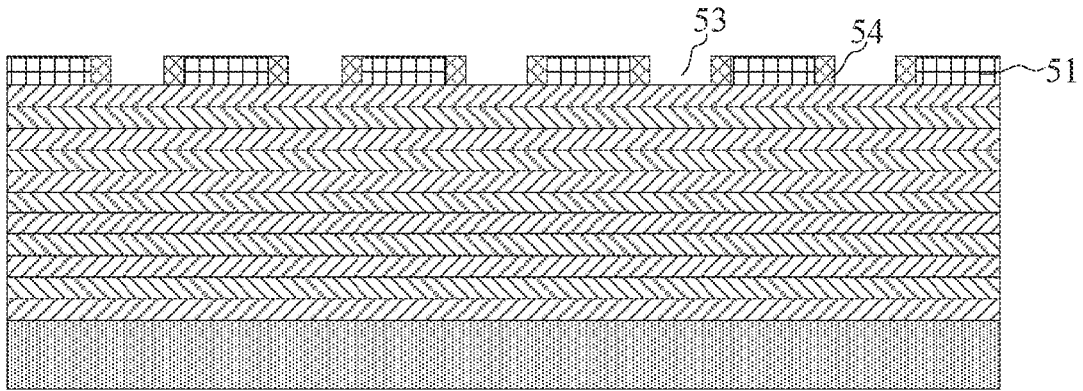
Figure 8:
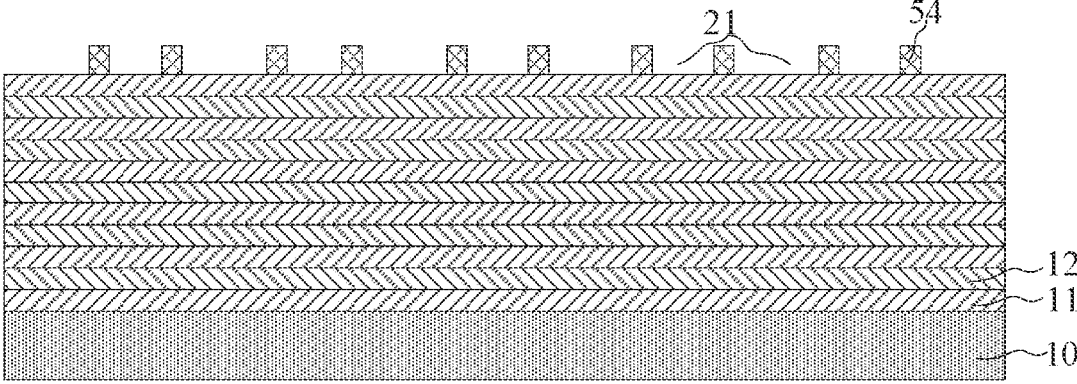

10—Substrate; 11—First material layer; 12—Second material layer; 20—Mask; 21—Slot; 30—molding material; 40—Nanopore; 51—Transition mask; 52—Photoresist; 53—Transition slot; 54—Spacer.

DETAILED DESCRIPTION OF EMBODIMENTS

In order to make the objectives, technical solutions, and advantages of embodiments of the present disclosure clearer, the technical solutions in the embodiments of the present disclosure will be described clearly and completely with reference to the accompanying drawings. Apparently, the embodiments described are only some embodiments of the present disclosure, rather than all embodiments. Based on the described embodiments of the present disclosure, all other embodiments derived by those of ordinary skill in the art without creative labor, fall within the scope of protection of the present disclosure.

In order to facilitate the understanding of a method for manufacturing a nanostructure provided by the embodiments of the present disclosure, the following will first explain application scenarios of the method for manufacturing the nanostructure provided by the embodiments of the present disclosure. The method for manufacturing the nanostructure is applied to a process of manufacturing a nanopore array. The method for manufacturing the nanostructure will be described in detail with reference to the accompanying drawings below.

With reference to FIG. 1, the method for manufacturing the nanostructure provided by the embodiments of the present disclosure includes steps as follows.

In step S10, a substrate 10 is provided.

In step S20, a first material layer 11 and a second material layer 12 are alternately and periodically stacked on the substrate 10 to form a stacked layer. An etching selection ratio between the first material layer 11 and the second material layer 12 is not equal to 1.

In step S30, a mask 20 is formed on an upper surface of the stacked layer, and a pattern of slots 21 is formed in the mask 20. The pattern of the slots 21 includes a plurality of parallel slots 21, and each slot 21 has the upper surface of the stacked layer as a bottom.

In step S40, the stacked layer is etched from top to bottom, to an upper surface of the substrate 10, so as to transfer the pattern of the slots 21 to the stacked layer.

In step S50, the pattern of the slots 21 in the stacked layer is filled with a molding material 30, and the molding material 30 is planarized to the upper surface of the stacked layer.

In step S60, the first material layer 11 or the second material layer 12 left in the stacked layer is removed, so as to form nanopores 40 which are arranged in an array in the stacked layer.

According to the method described above, first, the stacked layer is formed by alternately and periodically stacking the first material layer 11 and the second material layer 12 on the substrate 10. Then, the pattern of the slots 21 is formed on the upper surface of the stacked layer, and the stacked layer is etched to the upper surface of the substrate 10, so as to transfer the pattern of the slots 21 to the stacked layer. Next, the pattern of the slots 21 in the stacked layer is filled with the molding material 30, and the first material layer 11 or the second material layer 12 left in the stacked layer is removed, so as to form the nanopores 40 arranged in the array in the stacked layer. Compared with the existing methods, the above method may not only ensure that the nanopores 40 are arranged in a regular geometric array, but also control diameters of the nanopores 40 and a density of the nanopores 40 by adjusting a spacing between slots 21 of the pattern of the slots 21, a thickness of the first material layer 11 and a thickness of the second material layer 12. The following will provide a detailed introduction to the above steps with reference to the accompanying drawings.

First, with reference to FIG. 1 and FIG. 2, the substrate 10 is provided. The substrate 10 may be a silicon substrate 10 or a substrate 10 of other materials. An upper surface of the substrate 10 has a flat surface area. The substrate 10 may be rectangular or circular. Preferably, a rectangular substrate 10 may be used.

Next, with reference to FIG. 1 and FIG. 2, the stacked layer is formed by alternately and periodically stacking the first material layer 11 and the second material layer 12 on the substrate 10. The etching selection ratio between the first material layer 11 and the second material layer 12 is not equal to 1. When the first material layer 11 and the second material layer 12 that are alternately stacked are formed, as shown in FIG. 2, a first material layer 11 may be first deposited on the substrate 10, then a second material layer 12 is deposited on the first material layer 11, and next, another first material layer 11 is deposited on the second material layer 12, so that the first material layer 11 and the second material layer 12 grow alternately and periodically. It should be noted that the number of the first material layers 11 in the stacked layer may be equal or unequal to the number of the second material layers 12 in the stacked layer. As shown in FIG. 2, the number of the first material layer 11 is one more than the number of the second material layer 12.

When selecting a material of the first material layer 11 and a material of the second material layer 12, the material of the first material layer 11 and the material of the second material layer 12 may be silicon and a silicon germanium material, respectively, so that an etching selection ratio between the two material layers is large. It is worth noting that the material selection for the first material layer 11 and the second material layer 12 are not limited to the silicon or silicon germanium materials mentioned above, and other material selection may be used.

For example, the material of the first material layer 11 may be a silicon germanium material, and the material of the second material layer 12 may be silicon, so as to facilitate deposition and etching of the first material layer 11 and second material layer 12 by using semiconductor deposition and etching processes. In this case, a concentration of germanium in the silicon germanium material may be any value between 5% and 100%, such as 5%, 10%, 20%, 30%, 40%, 50%, 60%, 70%, 80%, 90%, and 100%, so that the first material layer 11 and the second material layer 12 have a large etching selectivity ratio, facilitating a removal of the first material layer 11 or the second material layer 12 by using a selective etching process. In some embodiments, a concentration of germanium in the silicon germanium mate- rial may be any value between 5% (inclusive) and 100% (non-inclusive).

In addition, the thickness of the first material layer 11 and the thickness of the second material layer 12 may both be between 0.5 nm and 100 nm. Specifically, the thickness of the first material layer 11 and the thickness of the second material layer 12 may be any value between 0.5 nm and 100 nm, such as 0.5 nm, 5 nm, 15 nm, 25 nm, 35 nm, 45 nm, 55 nm, 65 nm, 75 nm, 85 nm, 95 nm, and 100 nm. It is worth noting that diameters of the nanopores 40 in a vertical direction and a distribution density of the nanopores 40 in the vertical direction may be adjusted by adjusting the thickness of the first material layer 11 and the thickness of the second material layer 12. Taking the examples shown in FIGS. 2 to 11, the second material layers 12 left are etched off to form nanopores 40. In this case, the larger the thickness of the first material layer 11, the smaller the density of the nanopores 40 distributed in the vertical direction; and the smaller the thickness of the first material layer 11, the larger the density of the nanopores 40 distrib- uted in the vertical direction. Also, in this case, the larger the thickness of the second material layer 12, the larger the diameter of the nanopore 40 in the vertical direction. The smaller the thickness of the second material layer 12, the smaller the diameter of the nanopore 40 in the vertical direction. A total number of the first material layers 11 and second material layers 12 in the stacked layer may be within a range of 2 layers to 1000 layers. That is, the total number of the first material layers 11 and second material layers 12 may be 3 layers, 100 layers, 300 layers, 500 layers, 800 layers, 1000 layers, etc., so that the diameters and density of the nanopores 40 may be adjusted over a large range.

Next, with reference to FIG. 1 and FIG. 3 to FIG. 8, a mask 20 is formed on the upper surface of the stacked layer, and the pattern of the slots 21 is formed in the mask 20. The pattern of the slots 21 includes a plurality of parallel slots 21, and each slot 21 has the upper surface of the stacked layer as a bottom. In this step, a spacing between two adjacent slots 21 in the pattern of the slots 21 may be adjusted, so that the diameter of the subsequently formed nanopore 40 in a horizontal direction may be adjusted. If the spacing between two adjacent slots 21 is small, the diameter of the formed nanopore 40 in the horizontal direction is small. If the spacing between two adjacent slots 21 is large, the diameter of the formed nanopore 40 in the horizontal direction is large. Correspondingly, the density of the nanopores 40 distributed in the horizontal direction may be adjusted by adjusting a width of the slot 21 in the pattern of the slots 21. If the width of the slot 21 is large, the density of the nanopores 40 distributed in the horizontal direction is small. If the width of the slot 21 is smaller, the density of the nanopore 40 distributed in the horizontal direction is large.

When forming the mask 20 on the upper surface of the stacked layer and forming the pattern of the slots 21 in the mask 20, a direct photolithography patterning process, a spacer patterning process or a photolithography plus spacer patterning process may be used, which may help to adjust the width of the slot 21 in the pattern of the slots 21, and in turn help to adjust the diameter of the formed nanopore 40. When using the direct photolithography patterning technol- ogy, the spacing and width of the formed slot 21 are limited by an accuracy of the photolithography process. When using the spacer patterning process, the spacing between slots 21 may be reduced by adjusting the number of times of the spacer transferring performed, thereby reducing the diam- eter of the nanopore 40 in the horizontal direction. Of course, the photolithography process may be integrated with the spacer patterning process, the mask 20 is formed on the upper surface of the stacked layer and the pattern of the slots 21 is formed in the mask 20 by using the photolithography plus spacer patterning process.

For example, as shown in FIG. 3 to FIG. 8, when forming the mask 20 on the upper surface of the stacked layer and forming the pattern of the slots 21 in the mask 20 by using the photolithography plus spacer patterning process, a tran- sition mask 51 may be deposited on the upper surface of the stacked layer, and the material of the transition mask 51 may be silicon nitride. Then, a pattern of transition slots 53 is formed in the transition mask 51 by using the direct pho- tolithography patterning process. The pattern of the transi- tion slots 53 includes a plurality of parallel transition slots 53, and each transition slot 53 has the upper surface of the stacked layer as a bottom. Specifically, the pattern of the transition slots 53 may be first transferred to a photoresist 52, and then, the pattern of the transition slots 53 is trans- ferred to the transition mask 51 by using an etching process (which may be a dry plasma etching process, etc.). Next, the mask 20 is deposited on a sidewall of the pattern of the transition slots 53 and a protruded surface between adjacent transition slots 53. Specifically, ALD, CVD, or LPCVD techniques may be used to deposit the mask 20 on the sidewall of the pattern of the transition slots 53 and the protruded surface between adjacent transition slots 53. A material of the mask 20 may be different from that of the transition mask 51, for example, the material of the mask 20 may be silicon dioxide, etc., which may facilitate subsequent selective etching to remove the transition mask 51 left. Next, the mask 20 is etched off on the protruded surface between the adjacent transition slots 53 by using an anisotropic etching process. Next, the transition mask 51 left is removed (where the transition mask 51 left may be etched off by using a process such as phosphoric acid wet etching), such that the mask 20 left serves as a pattern of spacers 54, and a slot 21 of the pattern of the slots 21 is formed between two adjacent spacers 54, which may help to form the nanopore 40 with a small diameter.

Figure 9:
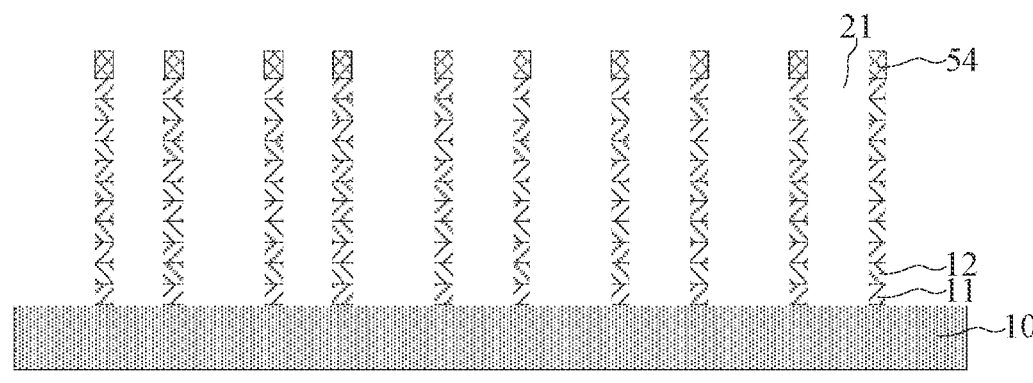

Next, with reference to FIG. 9, the stacked layer is etched from top to bottom, to the upper surface of the substrate 10, so as to transfer the slot 21 pattern to the stacked layer. Specifically, the stacked layer is etched from top to bottom, to the upper surface of substrate 10, by using a wet etching process and a phosphoric acid, or other etching solution may be used.

Figure 10:
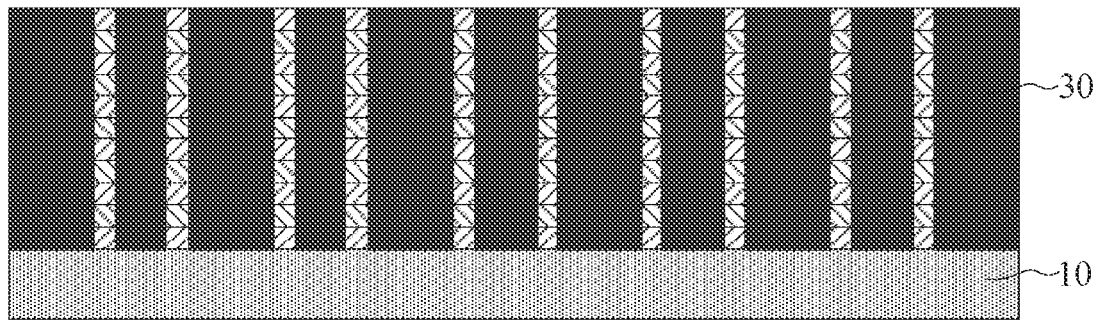

Next, with reference to FIG. 10, the pattern of the slots 21 in the stacked layer is filled with the molding material 30 and the molding material 30 is planarized to the upper surface of the stacked layer. Specifically, the molding material 30 may be silicon dioxide or aluminum oxide, so that the stiffness and stability of the formed nanostructure may be improved. Of course, other molding materials may also be used. After the molding material 30 is filled in the pattern of the slots 21, the molding material 30 is planarized by using a chemical mechanical grinding process until the upper surface of the stack is reached, and the spacers 54 are removed.

Figure 11:
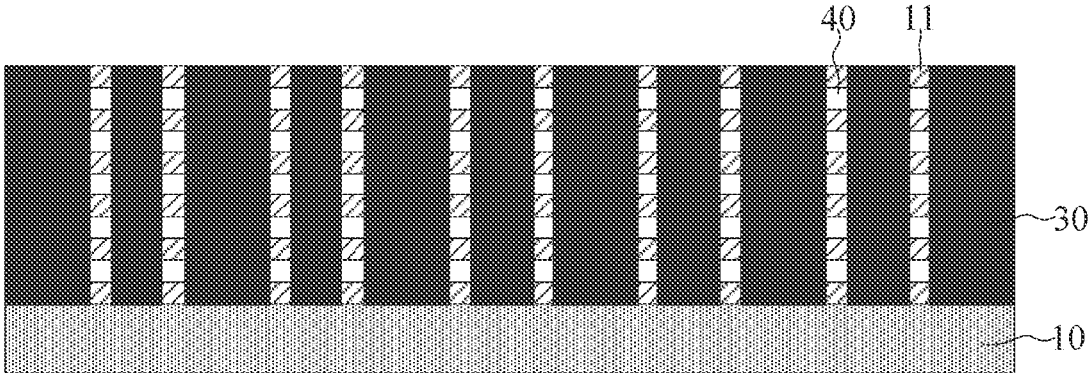

Next, with reference to FIG. 11, the first material layer 11 or the second material layer 12 left in the stacked layer is removed, so as to form the nanopores 40 arranged in an array in the stacked layer. For example, as shown in FIG. 11, the second material layers 12 left in the stacked layer are removed, so that the nanopores 40 arranged in an array is formed in the stacked layer. In FIG. 11, a direction in which the nanopore 40 extends is perpendicular to the paper surface.

For example, when removing the first material layer 11 or the second material layer 12 left in the stacked layer and forming the nanopores 40 arranged in an array in the stacked layer, a gas etching or a liquid etching may be used to remove the first material layer 11 or the second material layer 12 left in the stacked layer. Specifically, when removing the first material layer 11 or the second material layer 12 left in the stacked layer by using the gas etching method, an etching gas used in the gas etching is a mixed gas of $ClF_3$, $CF_4/O_2/He$, or a mixed gas of $NF_3/NH_3/O_2$, which may improve the efficiency and effectiveness of the gas etching. When removing the first material layer 11 or the second material layer 12 left in the stacked layer by using the liquid etching method, an etching liquid used in the liquid etching is a mixed liquid of $CH_3COOH/H_2O_2/HF$, which may improve the effectiveness and efficiency of the liquid etching.

As shown in FIG. 11, a cross-section of the nanopore manufactured by the above method is rectangular. As a more optimal implementation, the nanopore with a square cross-section may be manufactured by adjusting the thickness of the second material layer and the width of the spacer.

Figure 12:
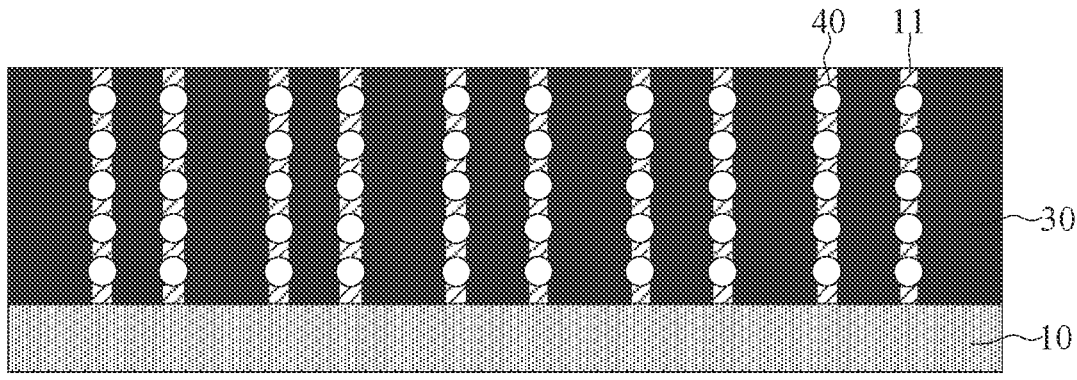

In addition, with reference to FIG. 11 and FIG. 12, the nanopore with the rectangular cross-section may further be rounded to obtain a nanopore with a circular cross-section, so as to meet corresponding requirements for use. When rounding the nanopore with the rectangular cross-section, corners of the rectangle are rounded by alternately performing oxidation treatment and removal of the oxidized layer. In the above oxidation treatment process, the semiconductor may be placed in a high-temperature environment, which has a temperature of 1050° C. and is filled with $O_2$, so as to oxidize the nanopore with the rectangular cross-section in the semiconductor to form the oxidized layer. Of course, other oxidation treatment methods may be used. For example, an oxygen plasma oxidation method may also be used at room temperature, and the oxidation may also be implemented by using a gas environment filled with $H_2O_2$, $O_3$, or $HNO_3$. The above-mentioned removal of the oxidized layer may be achieved by selectively removing the oxidized layer using HF at a ratio of 10:1 to 100:1. In the rounding process, the oxidation treatment and the removal of the oxidized layer may be alternately and periodically performed, so as to continuously adjust the nanopore with the rectangular cross-section until it becomes the nanopore with the circular cross-section.

Of course, other methods may be used for rounding the nanopore with the rectangular cross-section mentioned above. For example, an annealing process with $H_2$ at a temperature of 500° C. to 1000° C. may also eliminate the sharp corners of the rectangular cross-section and turn it into a circular cross-section, so as to form the nanopore with the circular cross-section.

It is worth noting that the principle of the above-mentioned rounding treatment is based on a spontaneous driving direction that a surface energy of the nanopore tends to decrease. Just as when putting a metal with burrs in a chemical solution, the metal with burrs is polished by corrosion, the rounding of the nanopore with the rectangular cross-section has the same mechanism.

In the various embodiments shown above, a stacked layer is formed by alternately and periodically stacking the first material layer 11 and the second material layer 12 on the substrate 10. Then, the pattern of the slots 21 is formed on the upper surface of the stacked layer, and the stacked layer is etched to the upper surface of the substrate 10, so as to transfer the pattern of the slots 21 to the stacked layer. Next, the pattern of the slots 21 in the stacked layer is filled with the molding material 30. The first material layer 11 or the second material layer 12 left in the stacked layer is removed, so as to form the nanopores 40 arranged in an array in the stacked layer. Compared with the existing methods, the method provided by the present disclosure is possible to not only ensure that the nanopores 40 are arranged in a regular geometric array, but also control diameters of the nanopores 40 and the density of the nanopores 40 by adjusting the spacing between slots 21 in the pattern of the slots 21, the thickness of the first material layer 11 and the thickness of the second material layer 12.

In addition, some embodiments of the present disclosure further provide a nanostructure, which is manufactured by using any of the above-mentioned methods for manufacturing a nanostructure. A stacked layer is formed by alternately and periodically stacking the first material layer 11 and the second material layer 12 on the substrate 10. Then, the pattern of the slots 21 is formed on the upper surface of the stacked layer, and the stacked layer is etched to the upper surface of the substrate 10, so as to transfer the pattern of the slots 21 to the stacked layer. Next, the pattern of the slots 21 in the stacked layer is filled with the molding material 30. The first material layer 11 or the second material layer 12 left in the stacked layer is removed, so as to form the nanopores 40 arranged in an array in the stacked layer. Compared the existing methods, the above-mentioned nanostructure is possible to not only ensure that the nanopores 40 are arranged in a regular geometric array, but also control diameters of the nanopores 40 and the density of the nanopores 40 by adjusting the spacing between slots 21 in the pattern of the slots 21, the thickness of the first material layer 11 and the thickness of the second material layer 12.

The above is only the specific embodiments of the present disclosure, however, the scope of protection of the present disclosure is not limited to this. Any changes or replacements that may easily be imagined by those familiar with the technical field within the scope of protection of the present disclosure should fall within the scope of protection of the present disclosure. Therefore, the scope of protection of the present disclosure should be based on the scope of protection of the claims.

What is claimed is:

1. A method for manufacturing a nanostructure, comprising:

providing a substrate;

alternately and periodically stacking a first material layer and a second material layer on the substrate to form a stacked layer, wherein an etching selection ratio between the first material layer and the second material layer is not equal to 1;

forming a mask on an upper surface of the stacked layer and forming a slot pattern in the mask, wherein the slot pattern comprises a plurality of parallel slots, and a bottom of each slot is defined by the upper surface of the stacked layer;

etching the stacked layer from top to bottom, to an upper surface of the substrate, so as to transfer the slot pattern to the stacked layer;

filling the slot pattern in the stacked layer with a molding material, and planarizing the molding material to the upper surface of the stacked layer; and removing the first material layer or the second material layer left in the stacked layer, so as to form nanopores arranged in an array in the stacked layer, wherein the nanopores are defined by the molding material and a remaining one of the first material layer and the second material layer that is not removed; and an extension direction of the nanopores is parallel to an extension direction of the slots.

2. The manufacturing method of claim 1, wherein the molding material is silicon dioxide or aluminum oxide.

3. The manufacturing method of claim 1, wherein a material of the first material layer is silicon germanium material, and a material of the second material layer is silicon.

4. The manufacturing method of claim 3, wherein an atomic concentration of germanium in the silicon germanium material is within a range of 5% to 100%.

5. The manufacturing method of claim 1, wherein a thickness of the first material layer is within a range of 0.5 nm to 100 nm, a thickness of the second material layer is within a range of 0.5 nm to 100 nm, and a total number of layers of the first material layer and second material layer comprised in the stacked layer is within a range of 2 layers to 1000 layers.

6. The manufacturing method of claim 1, wherein the removing the first material layer or the second material layer left in the stacked layer, so as to form nanopores arranged in an array in the stacked layer comprises:

removing the first material layer or the second material layer left in the stacked layer by using a gas etching method or a liquid etching method.

7. The manufacturing method of claim 6, wherein:

removing the first material layer or the second material layer left in the stacked layer comprises using the gas etching method, wherein an etching gas used in the gas etching is a mixed gas of $CIF_3$ and $CF_4/O_2/He$, or a mixed gas of $NF_3/NH_3/O_2$; or removing the first material layer or the second material layer left in the stacked layer comprises using the liquid etching method, wherein an etching liquid used in the liquid etching is a mixed liquid of $CH_3COOH/H_2O_2/HF$.

8. The manufacturing method of claim 1, wherein the forming a mask on an upper surface of the stacked layer and forming a slot pattern in the mask comprises:

forming the mask on the upper surface of the stacked layer and forming the slot pattern in the mask by using a direct photolithography patterning process, a spacer patterning process or a photolithography plus spacer patterning process.

9. The manufacturing method of claim 8, wherein the forming the mask on the upper surface of the stacked layer and forming the slot pattern in the mask comprises using the photolithography plus spacer patterning process, comprising:

depositing a transition mask on the upper surface of the stacked layer;

forming a transition slot pattern in the transition mask by using a direct photolithography patterning process, wherein the transition slot pattern comprises a plurality of parallel transition slots, and each transition slot has the upper surface of the stacked layer as a bottom;

depositing a mask on a sidewall of the transition slot pattern and a protruded surface between adjacent transition slots;

etching off the mask on the protruded surface between the adjacent transition slots by using an anisotropic etching process; and removing the transition mask left such that the mask left serves as a spacer, wherein a slot of the slot pattern is formed between two adjacent spacers.

* * * * *